United States Patent [19]

Schreuder

[11] Patent Number: 5,032,408

[45] Date of Patent: Jul. 16, 1991

[54] COMPOSITION FOR TREATMENT OF SKIN AFFECTIONS AND PROCESS FOR ITS PREPARATION

[75] Inventor: J. C. P. Schreuder, Baarn, Netherlands

[73] Assignee: Chemisch Adviesburea Drs. J.C.P. Schruder, Baarn, Netherlands

[21] Appl. No.: 865,266

[22] Filed: May 20, 1986

[30] Foreign Application Priority Data

May 28, 1985 [EP]  European Pat. Off. ......... 85106526.8

[51] Int. Cl.$^5$ .................... A61K 35/39; A61K 35/28; A61K 35/78
[52] U.S. Cl. .................... 424/556; 124/580; 124/195.1; 514/474; 514/558
[58] Field of Search ............ 424/95, 110, 195.1, 424/580, 556; 514/558, 861, 863, 864, 474

[56] References Cited

U.S. PATENT DOCUMENTS

| | | | |
|---|---|---|---|
| 2,153,653 | 4/1939 | Stux | 424/195.1 X |
| 4,263,284 | 4/1981 | Schreuder | 424/180 |
| 4,369,180 | 1/1983 | Mihalovits | 424/195.1 X |
| 4,446,051 | 5/1984 | Berthod et al. | 252/309 |
| 4,522,807 | 6/1985 | Kaplan | 424/59 |
| 4,783,332 | 11/1988 | Schreuder | 424/63 X |

FOREIGN PATENT DOCUMENTS

| | | |
|---|---|---|
| 0007120 | 1/1980 | European Pat. Off. |
| 0048153 | 3/1982 | European Pat. Off. |
| 0158090 | 10/1985 | European Pat. Off. |
| 2504551 | 10/1982 | France ........................ 424/195.1 |
| 2530466 | 1/1984 | France ........................ 424/95 |
| 0064909 | 4/1985 | Japan ........................ 424/110 |
| 1091133 | 5/1986 | Japan ........................ 424/110 |
| 0644481 | 1/1979 | U.S.S.R. ........................ 424/110 |

OTHER PUBLICATIONS

Richand, Chem. Abs. 80, 74270m, 1974.
Thuillier et al., Chem. Abs., 83, 33021z, 1975.
Webster's Ninth New Collegiate Dictionary, p. 219 (1986).
The Merck Manual of Diagnosis and Therapy, pp. 49-51 (1987).

*Primary Examiner*—John W. Rollins
*Attorney, Agent, or Firm*—Bierman and Muserlian

[57] ABSTRACT

The invention is directed to a composition of skin disorders, such as cellulites or striae, comprising
an oily fraction of paraffinic oils,
an emulsifier, predominantly consisting of
  a) mono- and/or diglycerides of higher unsaturated natural fatty acids, and
  b) ethoxylated glycerides esterified with fatty acids,
pancreas extract and/or thymus extract derived from pancreas and/or thymus tissue as such or from previously partially hydrolized pancreased and/or thymus tissue,
stabilizer consisting of montmorillonites, the free oxygen sites of which have been covered with quaternary groups,
a preservative consisting of esters of p-hydroxybenzoic acid and/or substituted imidazolidinyl urea derivatives, and
water.

10 Claims, No Drawings

COMPOSITION FOR TREATMENT OF SKIN AFFECTIONS AND PROCESS FOR ITS PREPARATION

The invention is relating to a composition for the treatment of skin affections and more particularly to a composition for treatment of so called skin disorders such as cellulitis or striae which affections seem both to be caused by a disturbed metabolism in the derm and usually manifest by means of an irregular shape of the epidermis and/or striking concentration of fatty tissue due to the absence or the destroyed state of connective tissue.

The invention is more relating to the application of such a composition for the fight against the beforementioned symptom and to a process for the preparation of such composition.

Already several means and compositions were proposed in the past for avoidance of such skin affections. However, with the formerly proposed means the prevention of the beforementioned symptoms could not be attained. Therefore there is a still growing need for compositions for an efficient and quick treatment of the beforementioned skin disorders.

Surprisingly there could be found, as result of extensive research and experimentation, an adequate composition, which comprises at least the following ingredients: an oily fraction, consisting of optionally branched paraffinic oils containing 10-30 carbon atoms and preferably 12-25 carbon atoms in their chain, in an amount of 5-50% by weight and preferably by 10-30% by weight, calculated on the weight of the complete composition. The paraffinic oils have a boiling range of between 100° and 500° C. and show a viscosity of up to 35 centistokes at 25° C.

These paraffinic oils may optionally be mixed with esters from predominantly unsaturated higher natural fatty acids and from higher natural unsaturated aliphatic alcohols containing at most 20 carbon atoms, such as oleyl oleate or oleyl decalate (e.g. Cetiol V ®).

By the term "higher natural fatty acids" and "higher natural" alcohols is meant fatty acids and alcohols, which may be derived from products occuring in nature, such as animal or vegetable oils and fats such as linseed oil, sunflower oil, rape-seed oil, whale oil, perilla seed oil, tung oil, castor oil.

It has appeared that for the most effective compositions, these esters have to be added to the paraffinic oil fraction in an amount of 1-6% by weight and preferably 2-5% by weight, calculated on the weight of the complete composition. an emulsifier, predominantly composed by a) mono- and/or diglycerides of higher unsaturated natural fatty acids, such as linoleic acid, oleic acid, linolenic acid, eleostearic acid, licanic acid, ricinoleic acid, petroselinic acid, vaccenic acid, arachidonic acid, cetoleic acid, erucic acid, selacholeic acid or palmitoleic acid or mixtures thereof, optionally mixed with those, derived from saturated higher natural fatty acids such as palmitic acid, lauric acid, myristic acid, stearic acid or mixtures thereof (e.g. Tegomuls ®) in an amount of 1-10% by weight and preferably 2-8% by weight, calculated on the weight of the complete composition, and b) ethoxylated glycerides, esterified with fatty acids according to the general formula:

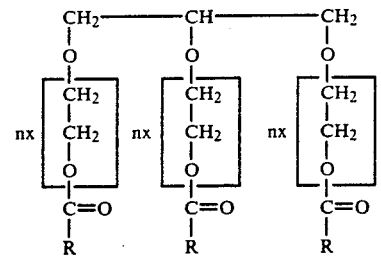

wherein n represents an integer from 5 to 20 and preferably 7-15, wherein R represents a saturated or unsaturated and preferably unsaturated fatty acid residue, derived from animal and/or vegetable oils, while R may represent the same or different fatty acid residues in one molecule but preferably the same residue (e.g. Tagat TO ®).

In contradistinction to a large number of systems of a different kind which were empirically tried for this purpose, the beforementioned emulsifier system surprisingly appeared to meet the requirement, that not too large amounts are used of the inevitably to be applied emulsifiers with reference to skin affections on the one hand, as relatively small amounts of this emulsifier system appeared to be necessary as compared with the presently proposed emulsifier system may be regarded according to the experience as extremely skin friendly which feature is related to a relatively low hydrophilic-lipophilic balance value.

The ratio between the amount of mono- and/or diglycerides on the one hand and the ethoxylated triglycerides on the other hand may vary, while the attractive activity is maintained, from 10-100 parts of mono- and/or diglycerides pro part of ethoxylated triglycerides and preferably 25 parts of mono- and/or diglycerides pro part of ethoxylated triglycerides. The total amount of the beforementioned emulsifier system, calculated on the weight of the complete composition may vary from 1-10% by weight and preferably from 2-8% by weight for the most attractive results. pancreas and/or thymus extract derived from pancreas and/or thymus tissue as such or from previously partially hydrolyzed pancreas and/or thymus tissue and more particular from bovine pancreas and/or thymus. The pancreas extract to be applied is used in an amount of 3-5% by weight as dry matter based on the weight of the total composition and preferably used as a standard solution containing 10% by weight of pancreas dry matter (e.g. Revitalin ®). Such a standard solution is added in an amount to give 0.05-5% by weight of pancreas dry matter material calculated on the weight of the complete composition and more preferably in an amount of 0.1-2% by weight.

The thymus extract is applied in an amount of 0.01-5% as dry matter based on the weight of the total composition and preferably used as a standard solution containing 2,5-4% by weight of dry matter and preferably 3-3,5% of thymus dry matter in the form of thymus hydrolysate (peptide). a stabilizer, consisting of montmorillonites, the free oxygen sites of which have been covered with quaternary groups.

Examples of such systems, which are preferably applied, are e.g. the so called Bentone ® and Propoloid ® preparations, which are added in an amount of 0.2-4% by weight and preferably of 0.5-2% by weight, calculated on the weight of the complete composition.

In the compositions containing the beforementioned stabilizers surprisingly no significant sagging occurs of one or more of the composing ingredients and particularly not in the relatively low viscous systems, which are preferred for practical reasons. a preservative. Preferably different types of preservatives are applied for the continoeus oily phase and the dispersed aqueous phase. For instance an ester of parahydroxy benzoic acid and preferably the methyl and/or the propyl and/or butyl ester in an amount of from 0.05–1% by weight, calculated on the weight of the complete composition and preferably in an amount of from 0.2–0.4% by weight are to be applied in the oily phase. Preferably mixtures of methyl-, propyl- and butyl-p-hydroxybenzoate are applied (e.g. Phenonip ®).

These beforementioned preservatives may be replaced in total or partially by other preservatives primarily consisting of imidazolidinyl urea derivatives (e.g. Euxyl ® or Hydroconserv ®) in an amount of from 0.05–1% by weight and preferably 0.2–0.4% by weight in the dispersed aqueous phase. water, ad 100% by weight, calculated on the weight of the complete composition.

In addition to the hereinbefore mentioned primary basic ingredients, one or more secondary ingredients may be added if desired, such as vitamin E as such or more preferably in the relatively stable acetate form, in an amount of 0.05–5% by weight based on the weight of the complete composition and more preferably in an amount of 0.2–2% by weight. glycerol as stabilizer of the emulsion, in an amount of 0.5–5.0% by weight calculated on the weight of the complete composition, and preferably in an amount of 1–3% by weight. carraghenate, in an amount of from 0.1 to 5% by weight, calculated on the weight of the complete composition and preferably in an amount of from 0.5–2% by weight.

The carraghenate, like e.g. Aubygum X ®, is preferably consisting of a polysaccharide bearing sulfonic acid residues, being of natural origin such as those derived from sea weeds. The sulfonic acid residues optionally have been converted into salts or esters e.g. sodium salt or ester from glycol, propylene glycol and glycerol (so called modified carraghenates).

Such carraghenates have empirically appeared to effect a surprisingly attractive stabilizing effect of the complete composition to be applied on the skin, while as additional advantageous effect, the known attractive properties of such carraghenates, such as elimination of an eventual hardening of tissue, appeared to be maintain in the final complete system.

The hereinbefore mentioned amounts of carraghenate cause in the final composition a gel structure with a viscosity of from 200–5000 centipoises which is desired for an adequate application.

It will be appreciated by a person skilled in the art of this specific area, that the carraghenate possibly may partially be replaced by alternative gel forming means such as carboxymethylcellulose esterified polyacrylic acid (such as Carbopol ®), hydroxy ethyl cellulose, in an amount which leads to a viscosity of the final composition in the same desired, hereinbefore mentioned specified range. perfume in an amount of from 0.1–0.5% by weight and preferably in an amount of 0.2% by weight, calculated on the amount of the total composition, an antioxydant in an amount of from 0.01–0.3% by weight and preferably in an amount of 0.1% by weight, calculated on the weight of the total composition. citric acid and optionally vitamin C, in an amount of 0.1–5% by weight calculated on the weight of the total composition and preferably in such an amount to give a pH of the total composition of a value from 5–8° and more particularly a normal pH of the outer skinlayers of from 5.5–7.5. It will be appreciated that the citric acid and/or vitamin C have to be added in the form of a buffer system, i.e. in partially neutralized form. alcohol (96%) in an amount of 0.1–1.0% by weight and preferably of 0.3–0.6% by weight, calculated on the weight of the total composition. The alcohol may be added for a fast gelation of the quaternary montmorillonites and preferably in an amount being the half of the amount of montmorillonites. camomile extract for giving the final composition the desired colour, in an amount of 0.01–0.5% by weight and preferably of 0.05–0.1% by weight, calculated on the weight of the complete composition (e.g. Azuleen ®).

The present compositions are characterized in a relatively low viscosity and high stability and a fast curing of the beforementioned skin affections.

The compositions according to the present invention may be prepared according to a process, which forms another feature of this invention, the sequence of the addition and the rate of dosage of the respective components and the temperature of which have appeared to be important.

According to this process in a first step the complete continuous oily phase is prepared, composed by respectively the oil fractions, the esters of unsaturated fatty acids and alcohols, emulsifiers, stabilizers, preservatives and alcohol, while the dispersed aqueous phase is composed by water, glycerol, pancreas extract, the carraghenate, citric acid and/or vitamin C. The vitamin E and camomile extract and perfume may be added to the prepared emulsion.

The final compositions of the present invention are preferably prepared by preparing and mixing the both phases at a temperature of at most 30° C., while adding of vitamin E, camomile extract and perfume and homogenizing the mixture.

The emulsion is additionally stirred and homogenized until an average size of the dispersed particles of at most 5µ and preferably <3µ is reached.

It will be appreciated, that the process is characterized in a significant simplicity, which means a saving of labour and/or energy and therefore leads to lowered costs.

It will be appreciated that the treatment of the beforementioned skin disorders with the present compositions has to be regarded as one of the features of the invention.

Such a treatment is carried out in a way, usual for such compositions and is more particularly carried out by a process, characterized in that an amount of 2–5 ml is applied on the skin area involved and is spread evenly, optionally after thorough and careful cleaning of the skin with water and soap and/or an alcoholic solution.

This treatment has preferably to be carried out 2–3 times a day.

An additional advantage of such a treatment is caused by the fact that the skin area involved is not greasy rather immediately after treatment due to a fast penetration of the composition into the skin tissue. Therefore smudges in clothes or bed-linen may be avoided.

The invention is illustrated on basis of the subsequent examples, however without restricting the scope of it thereto:

EXAMPLE 1

Under stirring the following ingredients are combined:

| | | |
|---|---|---|
| paraffinic oil (I) | 130 g. | |
| (Shell Ondina 15 ®, boiling range 295-390° C.) | | |
| paraffinic oil II | 30 g. | |
| (Shell Ondina 68 ®, boiling range 290-500° C.) | | |
| mono- and/or diglycerides (Tegomuls ®) | 25 g. | |
| oleyl decalate (Cetiol V ®) | 30 g. | oily phase |
| ethoxylated triglycerides (Tagat TO ®) | 1 g. | |
| preservative I (Phenonip ®) | 2 g. | |
| followed by addition of | | |
| quaternary modified montmorillonites (Bentone 38 ®) | 6 g. | |
| and gelation by | | |
| addition of alcohol (96%) | 3 g. | |

The mixture is cooled to at most 30° C.
In water (632.5 g.) are subsequently dissolved:

| | | |
|---|---|---|
| preservative II (Euxyl 100 ®) | 3 g. | |
| glycerol | 20 g. | |
| pancreas extract (Revitalin ® solution | 100 g. | aqueous phase |
| containing 10% by weight dry matter) | | |
| carraghenate (Aubygum X2 ®) | 5 g. | | giving an aqueous phase, which is subsequently mixed with the obtained oily phase and homogenized after addition of vitamin E (10 g.), camomile extract (0.5 g) and perfume (2 g.)

The obtained emulsion is further homogenized until an average particle size <3μ is reached.

EXAMPLE 2

In the same way as described under example 1, a composition is prepared from the following ingredients:

| | | |
|---|---|---|
| paraffinic oil I | 125 g. | |
| paraffinic oil II | 30 g. | |
| mono- and/or diglycerides | 16 g. | |
| oleyloleate | 26 g. | |
| ethoxylated triglycerides | 1 g. | oily phase |
| preservative I | 2 g. | |
| quaternary modified montmorillonites (Bentone 38 ®) | 6 g. | |
| alcohol (96%) | 3 g. | |
| and | | |
| water | 610 g. | |
| glycerol | 15 g. | |
| pancreas extract (Revitalin ®, 10% solution) | 150 g. | aqueous phase |
| preservative II | 3 g. | |
| carraghenate (Aubygum X2 ®) | 6 g. | |
| and | | |
| perfume | 1 g. | |
| vitamin E (acetate) | 5 g. | |
| camomile extract (azuleen) | 1 g. | |

EXAMPLE 3

In the same way as defined in example 1, a composition was prepared from the following ingredients:

| | | |
|---|---|---|
| paraffinic oil I | 160 g. | |
| paraffinic oil II | 35 g. | |
| mono- and/or diglycerides | 25 g. | |
| oleyldecalate | 26 g. | |
| ethoxylated triglycerides | 2 g. | oily phase |
| preservative I | 2 g. | |
| quaternary modified montmorillonites | 7 g. | |
| alcohol (96%) | 3 g. | |
| and | | |
| water | 510 g. | |
| citric acid buffer, corresponding with citric acid | 10 g. | |
| pancreas extract (Revitalin ®, 10% sol.) | 200 g. | aqueous phase |
| preservative III (Hydroconserv ®) | 3 g. | |
| carraghenate (Aubygum X2 ®) | 10 g. | |
| and | | |
| perfume | 1 g. | |
| vitamin E (acetate) | 5 g. | |
| camomile extract (azuleen) | 1 g. | |

EXAMPLE 4

In the same way as described in example 1, a composition was prepared from the following ingredients:

| | | |
|---|---|---|
| paraffinic oil I | 140 g. | |
| paraffinic oil II | 25 g. | |
| mono- and/or diglycerides | 15 g. | |
| oleyldecalate | 26 g. | oily phase |
| ethoxylated triglycerides | 0.5 g. | |
| preservative I | 3 g. | |
| quaternary modified montmorillonites | 7 g. | |
| alcohol (96%) | 3 g. | |
| and | | |
| water | 500.5 g. | |
| vitamin C and citric acid in a buffer form) | 15 g. | |
| glycerol | 20 g. | aqueous phase |
| pancreas extract (Revitalon ®, 10% sol.) | 200 g. | |
| preservative III | 3 g. | |
| carraghenate (Aubygum X2 ®) | 15 g. | |
| and | | |
| perfume | 1 g. | |
| vitamin E (acetate) | 25 g. | |

| -continued | |
|---|---|
| camomile extract | 1 g. |

EXAMPLE 5

In the same way as described in example 1, a composition was prepared from the following ingredients:

| paraffinic oil I | 130 g. | |
|---|---|---|
| paraffinic oil II | 30 g. | |
| mono- and/or diglycerides | 25 g. | |
| oleyl decalate | 30 g. | oily phase |
| ethoxylated triglycerides | 1 g. | |
| preservative I | 3 g. | |
| quaternary modified montmorillonites | 7 g. | |
| alcohol (96%) | 3 g. | |
| and | | |
| water | 666 g. | |
| citric acid in a buffer form | 15 g. | |
| glycerol | 20 g. | aqueous phase |
| thymus extract (3% solution) | 35 g. | |
| preservative II | 3 g. | |
| carraghenate | 15 g. | |
| and | | |
| perfume | 1 g. | |
| vitamine E (acetate) | 15 g. | |
| camomile extract | 1 g. | |

EXAMPLE 6

In the same way as described in example 1, a composition was prepared from the following ingredients:

| paraffinic oil I | 130 g. | |
|---|---|---|
| paraffinic oil II | 30 g. | |
| mono- and/or diglycerides | 25 g. | |
| oleyl decalate | 30 g. | oily phase |
| ethoxylated triglycerides | 1 g. | |
| preservative I | 3 g. | |
| quaternary modified montmorillonites | 7 g. | |
| alcohol (96%) | 3 g. | |
| and | | |
| water | 656 g. | |
| vitamin C and citric acid in a buffer form) | 15 g. | aqueous phase |
| glycerol | 18 g. | |
| thymus extract (3% solution) | 15 g. | |
| pancreas extract (10% solution) | 50 g. | |
| and | | |
| perfume | 1 g. | |
| vitamin E | 15 g. | |
| camomile extract | 1 g. | |

I claim:

1. Process for the preparation of a composition for the treatment of skin disorders consisting essentially of a continuous oily fraction consisting of branched or unbranched paraffinic oils containing 10 to 30 carbon atoms in the amount of 5% to 50% by weight, calculated on the weight of the complete composition and unmixed or mixed with esters of unsaturated higher natural fatty acids and higher natural unsaturated aliphatic IN THE alcohols both containing at most 20 carbon atoms, an emulsifier composed of a) at least one member of the group consisting of mono- and diglycerides of higher unsaturated natural fatty acids, unmixed or mixed with the esters derived from saturated higher natural fatty acids, in an amount of 1% to 10% by weight, calculated on the weight of the complete composition, and b) ethoxylated glycerides esterified with fatty acids of the formula

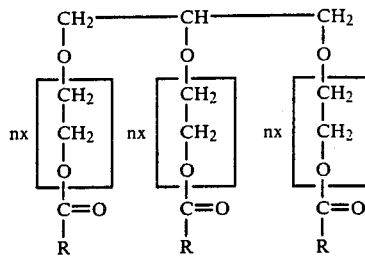

wherein n represents an integer from 5 to 20, R represents a saturated or unsaturated fatty acid residue derived from at least one member of the group consisting of animal and vegetable oils, and R may represent the same or different fatty acid residues in one molecule, whereby the ratio between the amount of mono- and diglycerides and the amount of ethoxylated triglycerides may vary from 10 to 100 parts of mono- and diglycerides per part of ethoxylated triglyceride, and whereby the amount of the emulsifier system, calculated on the weight of the complete composition may vary from 1% to 10% by weight, at least one member of the group consisting of pancreas extract and thymus extract derived from pancreas and thymus tissue and from previously partially hydrolyzed pancreas and thymus tissue, in an amount of 0.05% to 5% by weight of pancreas dry matter material and an amount of 0.01% to 5% by weight of thymus dry matter material, calculated on the weight of the complete composition, stabilizer consisting of montmorillonites, the free oxygen sites of which have been covered with quaternary groups, in an amount of 0.2% to 4% by weight, calculated on the weight of the complete composition, a preservative being at least one member of the group consisting of esters of para hydroxybenzoic acid and substituted imidazolidinyl urea derivatives in an amount of 0.05% to 1% by weight, calculated on the weight of the complete composition and water to make up 100% by weight based on the weight of the entire composition characterized in that an oily phase is prepared by addition of the emulsifier, preservative and stabilizer to the oil components under stirring and heating and gelating after addition of alcohol, followed by cooling to 30° C. or lower and followed by addition of an aqueous phase prepared by stirring in water, the following ingredients glycerol, pancreas extract, the carraghenate, citric acid and vitamin C, optional buffer at a temperature of at most 30° C. followed by addition under stirring perfume and camomile extract, until an average particle size of at most 5µ is reached.

2. A method of treating a skin disorder of a person comprising applying to the skin of a person with a skin disorder an amount of a composition for the treatment of skin disorders consisting essentially of a continuous oily fraction consisting of branched or unbranched paraffinic oils containing 10 to 30 carbon atoms in the amount of 5% to 50% by weight, calculated on the weight of the complete composition and unmixed or mixed with esters of unsaturated higher natural fatty acids and higher natural unsaturated aliphatic alcohols both containing at most 20 carbon atoms, an emulsifier composed of a) at least one member of the group consisting of mono- and diglycerides of higher unsaturated natural fatty acids, unmixed or mixed with the esters derived from saturated higher natural fatty acids, in an amount of 1% to 10% by weight, calculated on the weight of the complete composition, b) ethoxylated glycerides esterified with fatty acids of the formula

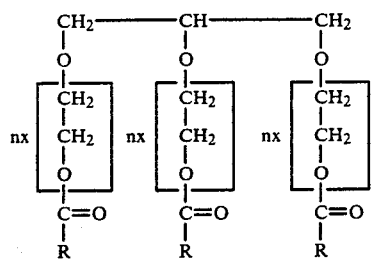

wherein n represents an integer from 5 to 20, R represents a saturated or unsaturated fatty acid residue derived from at least one member of the group consisting of animal and vegetable oils, and R may represent the same or different fatty acid residues in one molecule, whereby the ratio between the amount of mono- and diglycerides and the amount of ethoxylated triglycerides may vary from 10 to 100 parts of mono- and diglycerides per part of ethoxylated triglyceride, and whereby the amount of the emulsifier system, calculated on the weight of the complete composition may vary from 1% to 10% by weight, at least one member of the group consisting of pancreas extract and thymus extract derived from pancreas and thymus tissue and from previously partially hydrolyzed pancreas and thymus tissue, in an amount of 0.05% to 5% by weight of pancreas dry matter material and an amount of 0.01% to 5% by weight of thymus dry matter material, calculated on the weight of the complete composition, stabilizer consisting of montmorillonites, the free oxygen sites of which have been covered with quaternary groups, in an amount of 0.2% to 4% by weight, calculated on the weight of the complete composition, a preservative being at least one member of the group consisting of esters of para hydroxybenzoic acid and substituted imidazolidinyl urea derivatives in an amount of 0.05% to 1% by weight, calculated on the weight of the complete composition and water to make up 100% by weight based on the weight of the entire composition sufficient to treat the skin disorder.

3. The method of claim 2 wherein the skin disorder is cellulites or striae.

4. Method of claim 2, characterized in that it contains an oily fraction in an amount of 10-30% by weight of the composition.

5. Method of claim 2, characterized in that it is composed of an oily fraction, mixed with oleyl oleate or oleyl decalate, in an amount of 2-5% by weight, calculated on the weight of the composition of the complete composition.

6. Method of claim 2, characterized in that the emulsifier is composed of ethoxylated triglycerides and of mono- or diglycerides of mixtures thereof derived from linoleic acid, oleic acid, linolenic acid, or mixtures thereof, mixed with mono- or diglycerides or mixtures thereof derived from palmitic acid, or lauric acid, myristic acid, stearic acid or mixtures thereof.

7. Method of claim 2, characterized in that the ratio of mono- or diglycerides or mixtures thereof to the ethoxylated triglycerides is 25 parts per part ethoxylated triglycerides.

8. Method of claim 2, characterized in that preservative in the oily phase, one or more esters of p-hydroxybenzoic acid are applied in an amount of 0.2-0.4% by weight.

9. Method of claim 2, characterized in that preservative in the aqueous phase imidazolidinyl urea derivatives are applied in an amount of 0.2-0.4% by weight.

10. Method of claim 2, characterized in that the pH of the complete composition is between 5.5 and 7.5.

* * * * *